United States Patent [19]

Razavi

[11] Patent Number: 6,103,656

[45] Date of Patent: Aug. 15, 2000

[54] PROCESS FOR PREPARING AND USING MESO/RACEMIC-[BIS (INDENYL) ETHANE] ZIRCONIUM DICHLORIDE COMPOUNDS

[75] Inventor: Abbas Razavi, Mons, Belgium

[73] Assignee: Fina Research, S.A., Feluy, Belgium

[21] Appl. No.: 08/948,224

[22] Filed: Oct. 9, 1997

[51] Int. Cl.[7] ...................................................... B01J 31/22
[52] U.S. Cl. ............................ 502/152; 556/53; 502/120
[58] Field of Search ................................ 556/53; 502/152

[56] References Cited

U.S. PATENT DOCUMENTS

| 5,017,714 | 5/1991 | Welborn, Jr. .............................. 556/12 |
| 5,117,020 | 5/1992 | Razavi ..................................... 556/43 |
| 5,556,997 | 9/1996 | Strickler et al. .......................... 556/11 |
| 5,565,533 | 10/1996 | Galimberti et al. ..................... 526/127 |
| 5,849,653 | 12/1998 | Dall'Occo et al. ..................... 502/117 |

*Primary Examiner*—David W. Wu
*Assistant Examiner*—Caixia Lu
*Attorney, Agent, or Firm*—Jim Wheelington; M. Norwood Cheairs

[57] ABSTRACT

A process for the preparation of a meso/racemic-(bis (indenyl)ethane zirconium dichloride compound comprising (a) reacting zirconium tetrachloride with the solid reaction product of the bis(indenyl)ethane ligand with an alkyl-lithium in a solvent as reaction medium and (b) recovering a solid mixture of lithium chloride and meso/racemic composition of (bis(indenyl)ethane) zirconium dichloride, characterized in that the solvent used as reaction medium in a reaction (a) is an ether, pentane or a mixture thereof.

13 Claims, 3 Drawing Sheets

PROCESS FOR PREPARING AND USING MESO/RACEMIC-[BIS (INDENYL) ETHANE] ZIRCONIUM DICHLORIDE COMPOUNDS

BACKGROUND OF THE INVENTION

1. Field of the Invention

The present invention relates to a new process for preparing meso/racemic-[bis(indenyl)ethane]zirconium dichloride compounds and their use as catalysts in the polymerization or copolymerization of olefins.

2. Description of the Prior Art

The existing synthetic procedures for the preparation of meso/racemic-[bis(indenyl)ethane]zirconium dichlorides involve time consuming preparative and purifying steps, the catalyst prices being in the range of 8000–10000 U.S. dollars/kg. According to these procedures, the racemic isomer is formed as the main component since the aim of these procedures was to provide more and more (higher than 95%) of this racemic isomer for the ITP production purpose and it can be isolated after the purification with 99% of purity.

Thus there is a need in the art for an improved, modified and simple process to lower the Racemic catalyst production and to facilitate the accessibility of the meso isomer or highly meso enriched mixture of the two isomers. Additionally, an easy route for the separation of the two isomers is required to replace the conventional method of separation, i.e. the fractionation crystallization, which is not acceptable for the large scale catalyst production.

SUMMARY OF THE INVENTION

To this end, according to the present invention, said process which comprises the following steps :

(a) reacting zirconium tetrachloride with the solid reaction product of the bis(indenyl)ethane ligand with an alkyllithium in a solvent as reaction medium, and (b) recovering a solid mixture of lithium chloride and a meso/racemic composition of [bis(indenyl)ethane] zirconium dichloride, is characterized in that the solvent used as reaction medium in reaction (a) is an ether, pentane or a mixture thereof, more preferably diethyl ether.

According to an advantageous embodiment of the invention, the reaction (a) is carried out under stirring at a temperature from 15 to 30° C. and during a time period from 1 to 3 hours, preferably of about 2 hours.

According to another advantageous embodiment of the invention, said meso/racemic composition is separated from lithium chloride with an extractant solvent such as for example methyl chloride or dichloromethane.

This invention relates also to a process for the polymerization or copolymerization of olefins comprising contacting at least one olefinic monomer in the presence of a catalyst of a meso/racemic-[bis(indenyl)ethane]zirconium dichloride compound such as prepared.

BRIEF DESCRIPTION OF THE DRAWINGS

A more complete appreciation of the invention and many of the attendant advantages thereof will be readily understood by reference to the following detailed description when considered in connection with the accompanying drawings wherein.

In the drawings.

DETAILED DESCRIPTION OF THE INVENTION

Figure 1:
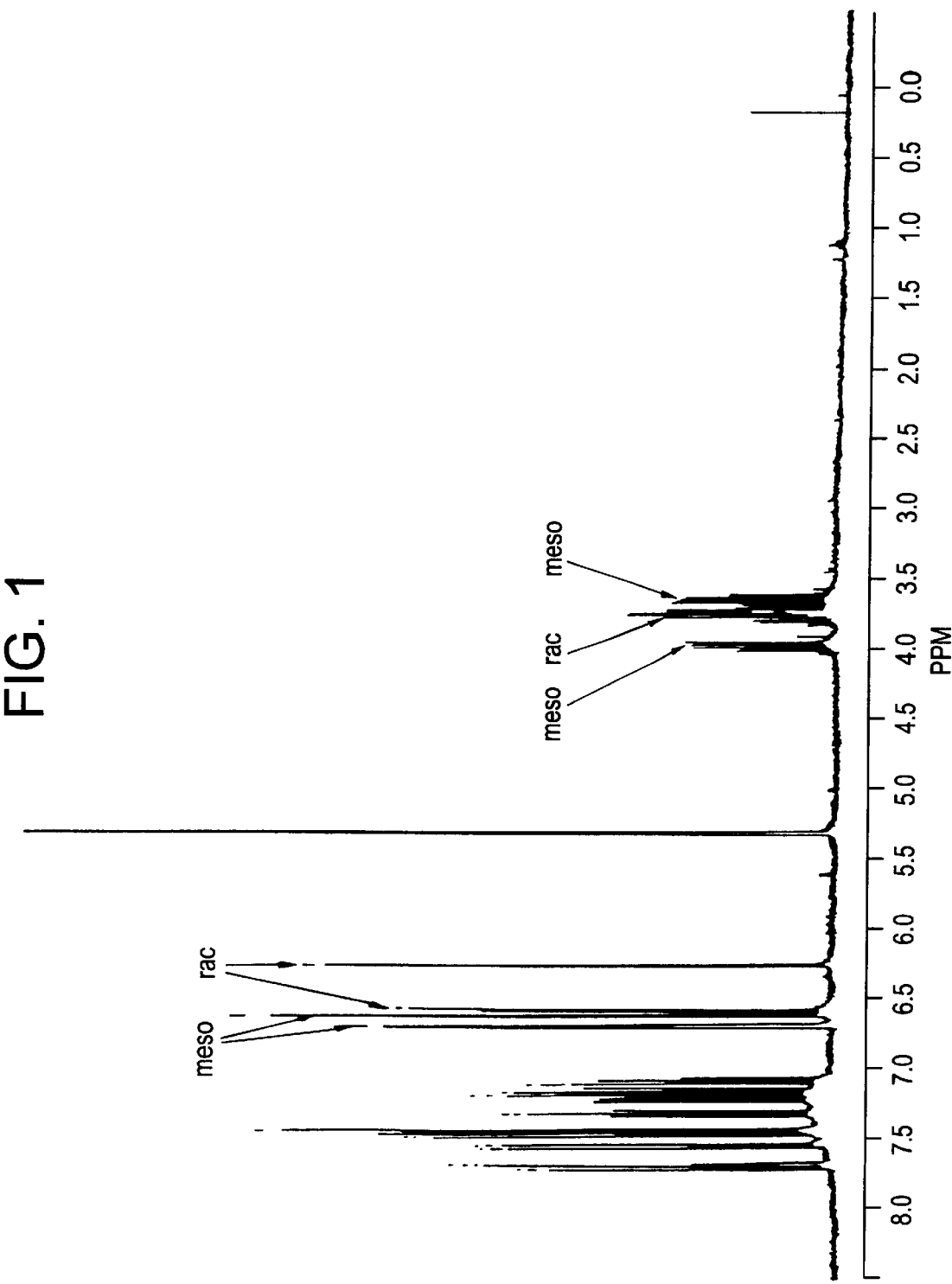
FIG. 1 represents the $^1$H-NMR spectrum of a meso/racemic metallocene of 50/50 prepared by the process of the invention.

Further details and features of the invention will be evident from the description given below by way of a non-limiting example of several particular embodiments of the invention.

As has already been indicated above the meso/racemic-[bis(indenyl)ethane]ZrCl$_2$ metallocenes of the invention are obtained by reacting zirconium tetrachloride with the solid reaction product of the bis(indenyl)ethane ligand with an alkyllithium in an ether, preferably diethyl ether, pentane or a mixture thereof, as reaction medium and by recovering a solid mixture of lithium salt and of the meso/racemic compound, the reaction between ZrCl$_4$ and the above mentioned solid reaction product being conducted under stirring at a temperature from 15 to 30° C., room temperature (about 25° C.) being preferred for obvious reasons. As one of ordinary skill in the art knows, lowering the temperature will require a longer reaction time, while increasing the temperature may result in a complete evaporation of the reaction solvent. The duration of reaction is generally between 1 and 3 hours, preferably of the order of about 2 hours. The reaction pressure is usually atmospheric. As known in the art, dry and oxygen-free conditions are required for this type of reaction and for the storage of the metallocenes.

The ligand may be prepared by using various methods well known in the art, depending on the selection of the specific substituents.

The reaction of the ligand with an alkyllithium is also well known in the art; it is generally carried out by dropwise addition of an alkyllithium solution in a solution of the ligand. Methyllithium and n-butyllithium are most often used, as are stoichiometric ratios of the reactants. The solid reaction product may be recovered by complete evaporation of the solvent. During the evaporation conditions, said product may have to be reduced to a fine powder, e.g. by grinding in a mortar.

After completion of the reaction step between ZnCl$_4$ and the solid reaction product of the ligand with alkyllithium, the reaction solvent is decanted and a solid mixture of lithium chloride and the isomeric metallocene is collected.

Then the metallocene is separated from the lithium salt with an extractant solvent. Suitable solvents are methyl chloride and dichloromethane. Thus the process of the invention provides a quantitative yield of the meso/racemic-(bisindenyl)ZrCl$_2$ mixture with an isomeric ratio of meso/rac=50/50 within a short time. Furthermore, the presence of high percentage of the meso isomer in the original crude mixture now allows its separation by a simple solvent extraction. In this way, meso/rac ratios close to 75/25 can be obtained without difficulty.

According to the present invention, there is also provided a process for the polymerization or copolymerization of olefins comprising contacting one or more olefinic monomers such as ethylene or propylene in the presence as catalyst of an isomeric metallocene such as obtained hereinabove.

The isomeric metallocene catalyst can be used in a supported form. Suitable supports are silicae having a surface area comprised between 200 and 600 m²/g and a pore volume comprised between 0.5 and 4.5 ml/g.

The invention having been generally described, the following examples are given as particular embodiments of the invention and to demonstrate the practice and advantages thereof. It is understood that the examples are given by way of illustration and are not intended to limit the specification or the claims to follow in any manner.

The invention will be now described by two examples according to the invention.

EXAMPLE 1 a. Reaction of the ligand with alkyllithium (synthesis of the dianion)

In a 500 ml round bottom flask equipped with addition funnel and magnetic stirring bar 5 g of the 1,2-bisindenylethane ligand is suspended in 100 ml of diethyl ether. Immediately after, under constant stirring, a solution of two equimol methyllithium in ether is added in a 10 min period. After an hour the gas evolution is ceased and the reaction is practically completed. The mixture is stirred for one more hour at ambient temperature and then the stirring is stopped, the supernatant ether is decanted and the dianion is isolated as a white solid.

b. Reaction of $ZrCl_4$ with the lithiated ligand (synthesis of the metallocene)

Figure 2:
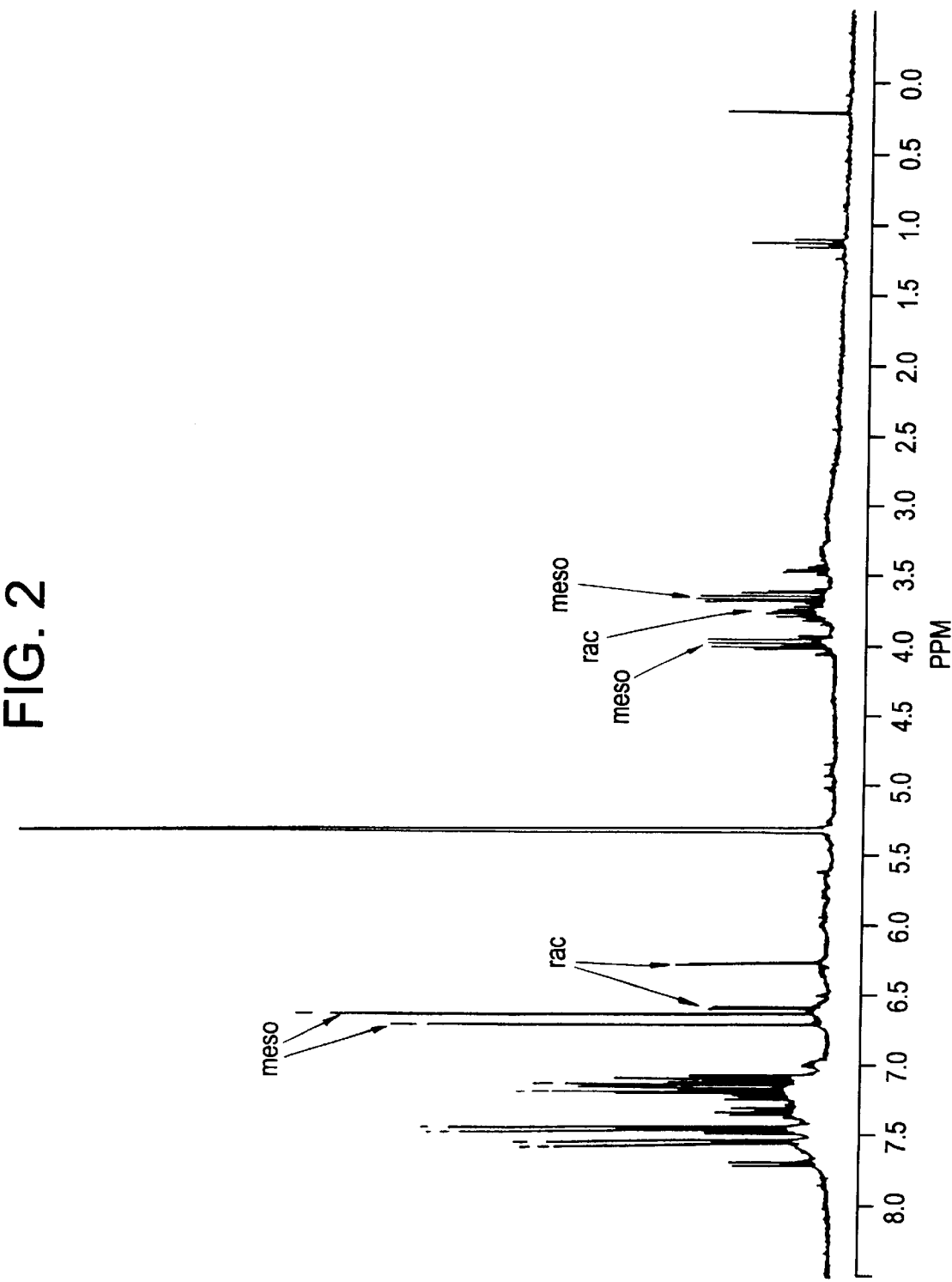
FIG. 2 represents the $^1$H-NMR spectrum of a meso/racemic metallocene of 75/25 prepared by the process of the invention.

To the white dianion obtained above, 4.8 g of $ZrCl_4$ suspended in 200 ml of diethyl ether is added under stirring. The color of the reaction mixture changes from white to yellow-orange instantly. After two hours the ether is decanted and a yellow-orange solid consisting of the isomeric metallocene and LiCl is collected. The metallocene is separated from LiCl with the aid of methyl chloride. According to the $^1$H-NMR spectrum (FIG. 1) of the crude product, a meso/racemic composition of 50/50 is formed quantitatively and it is of spectroscopic purity. Due to the higher solubility of the meso isomer in dichloromethane a simple solvent extraction provides a sample with a meso/racemic composition of 75/25 (FIG. 2).

EXAMPLE 2

Figure 3:
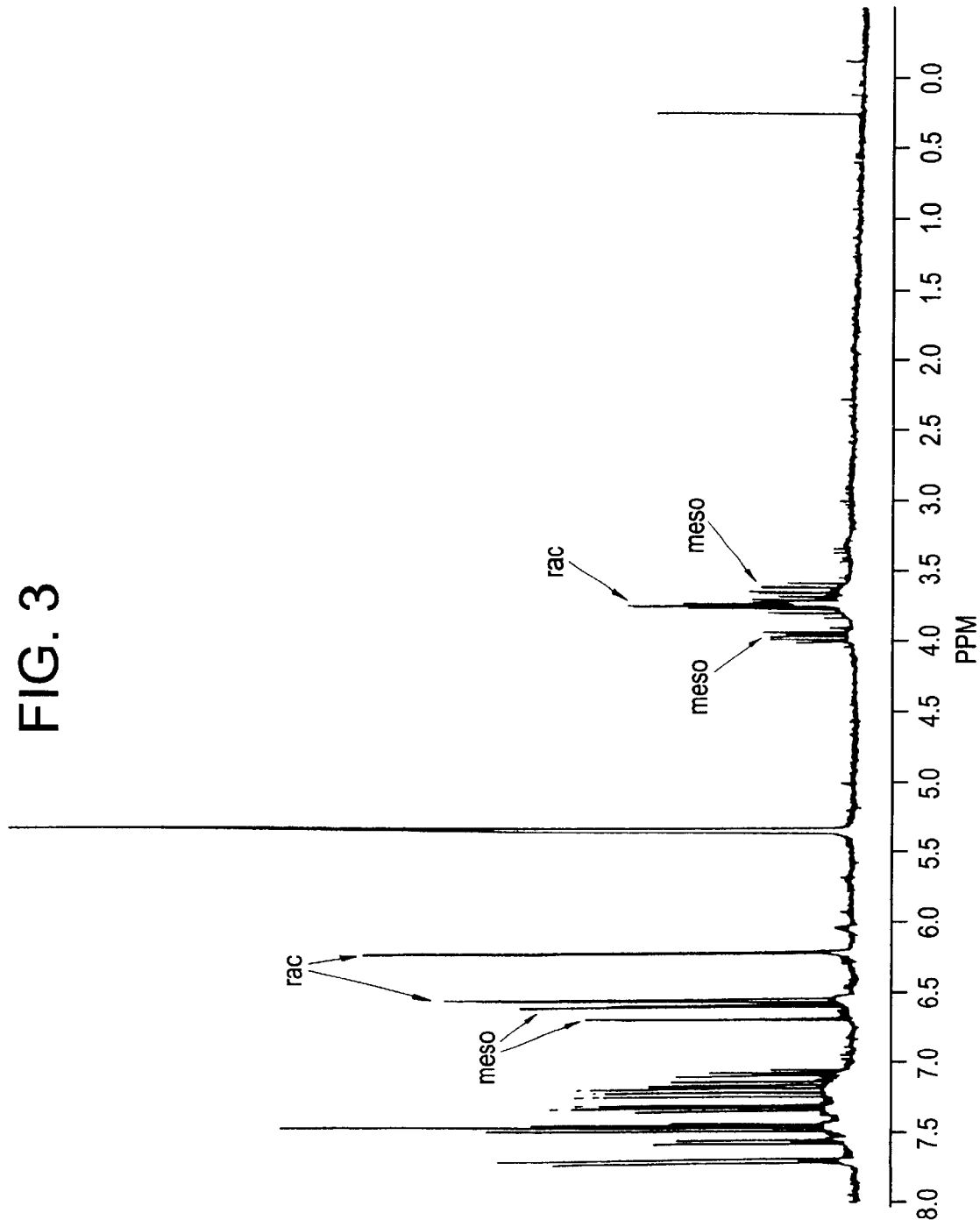
FIG. 3 represents the $^1$H-NMR spectrum of a meso/racemic metallocene of 50/50 prepared by the process of the invention.

To the white dianion described above in a) of the Example, 4.8 g of $ZrCl_4$ suspended in pentane is added. The reaction mixture is stirred for two more hours at room temperature. At the end of this period, the yellow-orange solid is filtered and extracted with methylene chloride to separate the LiCl by-product. The isomer composition and the yield is substantially the same as the ether procedure but the crude product contains some impurities (see FIG. 3).

The simplicity and rapidity of the process of the invention and the high meso content of the end product show that all the set objectives are attained. 100% pure meso isomer can be obtained when products in large scale are synthesized. It is possible to produce by this process supported catalyst with a (bisindenyl)$ZrCl_2$ metallocene with 50/50 and 75/25 isomeric ratios without any problems. Since a large part of racemic isomer is converted to the meso isomer during supporting reaction the final supported catalyst can have up to 85/15 meso/rac composition.

Nevertheless, the presence of such quantities of racemic isomer may be beneficial to the mechanical and optical properties of the polyethylene or polypropylene film obtained since it would give rise to a high molecular weight tailing in the distribution.

The process of the present invention can be also extended to other bis(indenyl)ethane)$ZrCl_2$ complexes with different substituents, in particular those with 2,2'-substituted and 2,2',4,4'-substituted indenyl ligands.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A process for the preparation of a meso/racemic-(bis (indenyl)ethane)zirconium dichloride compound comprising (a) reacting a bis(indenyl)ethane ligand with an alkyllithium to obtain a solid reaction product;

(b) reacting zirconium tetrachloride with the solid reaction product in a solvent as reaction medium; and (c) recovering a solid mixture of lithium chloride and a meso/racemic composition of (bis(indenyl)ethane) zirconium dichloride wherein the solvent used as reaction medium in step (b) is an ether, pentane or a mixture thereof.

2. A process according to claim 1, wherein the ether is diethyl ether.

3. A process according to claim 1, wherein the reaction (a) is carried out under stirring at a temperature from 15 to 30° C.

4. A process according to claim 3, wherein the duration of said reaction (a) is between 1 and 3 hours.

5. A process according to claim 4, wherein said duration is of about 2 hours.

6. A process according claims 1, wherein the reaction product of the ligand with an alkyllithium is added as a powder.

7. A process according claim 1, wherein the process further comprises separating the meso/racemic composition from lithium chloride with an extractant solvent.

8. A process according to claim 7, wherein the extractant solvent is methyl chloride or dichloromethane.

9. A process according to claim 8, wherein the extractant solvent is methyl chloride in order to obtain a meso/racemic composition of 50/50.

10. A process according to claim 8, wherein the extractant solvent is dichloromethane in order to obtain a meso/ racemic composition of 75/25.

11. A process according to claims 1, wherein the bis (indenyl)ethane ligand is selected from the 2,2'-substituted and 2,2',4,4'-substituted indenyl ligands.

12. A process according to claim 1 additionally comprising supporting the meso/racemic-[bis(indenyl)ethane] zirconium dichloride compound on a support.

13. A process according to claim 12, wherein the support is a silica having a surface area comprised between 200 and 600 m²/g and a pore volume comprised between 0.5 and 4.5 ml/g.

* * * * *